United States Patent
Kim et al.

(10) Patent No.: US 11,131,925 B2
(45) Date of Patent: Sep. 28, 2021

(54) WATER-SOLUBLE DIACETYLENE, PHOTOLITHOGRAPHY COMPOSITION COMPRISING WATER-SOLUBLE DIACETYLENE MONOMER AND CONDUCTIVE POLYMER, AND FINE PATTERN PREPARATION METHOD USING SAME

(71) Applicant: Industry-University Cooperation Foundation Hanyang University, Seoul (KR)

(72) Inventors: Jongman Kim, Seoul (KR); Chanwoo Lee, Seoul (KR); Taegeun Kim, Daejeon (KR); Kyungchan Uh, Bucheon-si (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 180 days.

(21) Appl. No.: 16/098,358

(22) PCT Filed: Apr. 26, 2017

(86) PCT No.: PCT/KR2017/004458
§ 371 (c)(1),
(2) Date: Nov. 1, 2018

(87) PCT Pub. No.: WO2017/191932
PCT Pub. Date: Nov. 9, 2017

(65) Prior Publication Data
US 2019/0144379 A1 May 16, 2019

(30) Foreign Application Priority Data
May 2, 2016 (KR) .......................... 10-2016-0054161

(51) Int. Cl.
*G03F 7/025* (2006.01)
*G03F 7/038* (2006.01)
(Continued)

(52) U.S. Cl.
CPC ............ *G03F 7/025* (2013.01); *C07C 303/22* (2013.01); *C07C 303/24* (2013.01);
(Continued)

(58) Field of Classification Search
CPC . G03F 7/025; G03F 7/405; G03F 7/32; C07C 305/04; C07C 309/51
See application file for complete search history.

(56) References Cited

U.S. PATENT DOCUMENTS 4,562,141 A * 12/1985 Tieke ...................... G03F 7/025
252/600
4,581,315 A 4/1986 Garito
4,798,740 A * 1/1989 Tomida ................... G03F 7/025
264/104

FOREIGN PATENT DOCUMENTS

| JP | 2014-152320 A | 8/2014 |
|---|---|---|
| KR | 10-2009-0008694 A | 1/2009 |
| WO | 98/37902 A1 | 9/1998 |

OTHER PUBLICATIONS

Richard E. Bruehl et al., "Polymerized Liposome Assemblies: Bifunctional Macromolecular Selectin Inhibitors Mimicking Physiological Selectin Ligands", Biochemistry, 2001, pp. 5964-5974, vol. 40, No. 20.
(Continued)

*Primary Examiner* — John S Chu
(74) *Attorney, Agent, or Firm* — Sughrue Mion, PLLC

(57) ABSTRACT

Provided are a novel water-soluble diacetylene monomer, a composition for photolithography including the novel water-soluble diacetylene monomer and a conductive polymer, and a method of forming micropatterns using the composition.
(Continued)

The water-soluble diacetylene monomer may not aggregate even when mixed with a water-soluble conductive polymer. Accordingly, a uniform composition for photolithography can be prepared by mixing a water-soluble conductive polymer with the diacetylene monomer, and micropatterns can be formed using the composition. More particularly, when the composition is formed into a thin film and then is irradiated with light, only light-irradiated portions of the diacetylene monomer are selectively crosslinked due to photopolymerization, thereby resulting in insoluble negative-type micropatterns.

10 Claims, 8 Drawing Sheets

(51) Int. Cl.
| | |
|---|---|
| G03F 7/32 | (2006.01) |
| G03F 7/40 | (2006.01) |
| C07C 303/24 | (2006.01) |
| C08L 81/02 | (2006.01) |
| C07C 303/42 | (2006.01) |
| C08F 2/48 | (2006.01) |
| C07C 305/14 | (2006.01) |
| H01L 51/00 | (2006.01) |
| C07C 313/04 | (2006.01) |
| C08F 38/00 | (2006.01) |
| G03F 7/09 | (2006.01) |
| C07C 303/22 | (2006.01) |
| C07C 305/04 | (2006.01) |
| C07C 309/51 | (2006.01) |
| C09D 5/24 | (2006.01) |
| C09D 165/00 | (2006.01) |
| G03F 7/004 | (2006.01) |
| G03F 7/16 | (2006.01) |
| G03F 7/20 | (2006.01) |
| H01L 51/10 | (2006.01) |
| H01L 51/44 | (2006.01) |
| H01L 51/52 | (2006.01) |

(52) U.S. Cl.
CPC .......... *C07C 303/42* (2013.01); *C07C 305/04* (2013.01); *C07C 305/14* (2013.01); *C07C 309/51* (2013.01); *C07C 313/04* (2013.01); *C08F 2/48* (2013.01); *C08F 38/00* (2013.01); *C08L 81/02* (2013.01); *C09D 5/24* (2013.01); *C09D 165/00* (2013.01); *G03F 7/0045* (2013.01); *G03F 7/038* (2013.01); *G03F 7/093* (2013.01); *G03F 7/162* (2013.01); *G03F 7/2004* (2013.01); *G03F 7/32* (2013.01); *G03F 7/405* (2013.01); *H01L 51/0023* (2013.01); *H01L 51/0035* (2013.01); *H01L 51/102* (2013.01); *H01L 51/441* (2013.01); *H01L 51/5206* (2013.01); *H01L 51/5221* (2013.01); C08G 2261/135 (2013.01); C08G 2261/1424 (2013.01); C08G 2261/3223 (2013.01); C08G 2261/76 (2013.01); *H01L 51/0037* (2013.01); *H01L 2251/5338* (2013.01)

(56) References Cited

OTHER PUBLICATIONS

Ramendra K. Pal et al., "Photolithographic Micropatterning of Conducting Polymers on Flexible Silk Matrices", Advanced Materials, 2016, pp. 1406-1412, vol. 28.

Yijie Xia et al., "Solution-Processed Metallic Conducting Polymer Films as Transparent Electrode of Optoelectronic Devices", Advanced Materials, 2012, pp. 2436-2440, vol. 24.

International Search Report for PCT/KR2017/004458 dated Jul. 26, 2017 (PCT/ISA/210).

* cited by examiner

[FIG. 1]
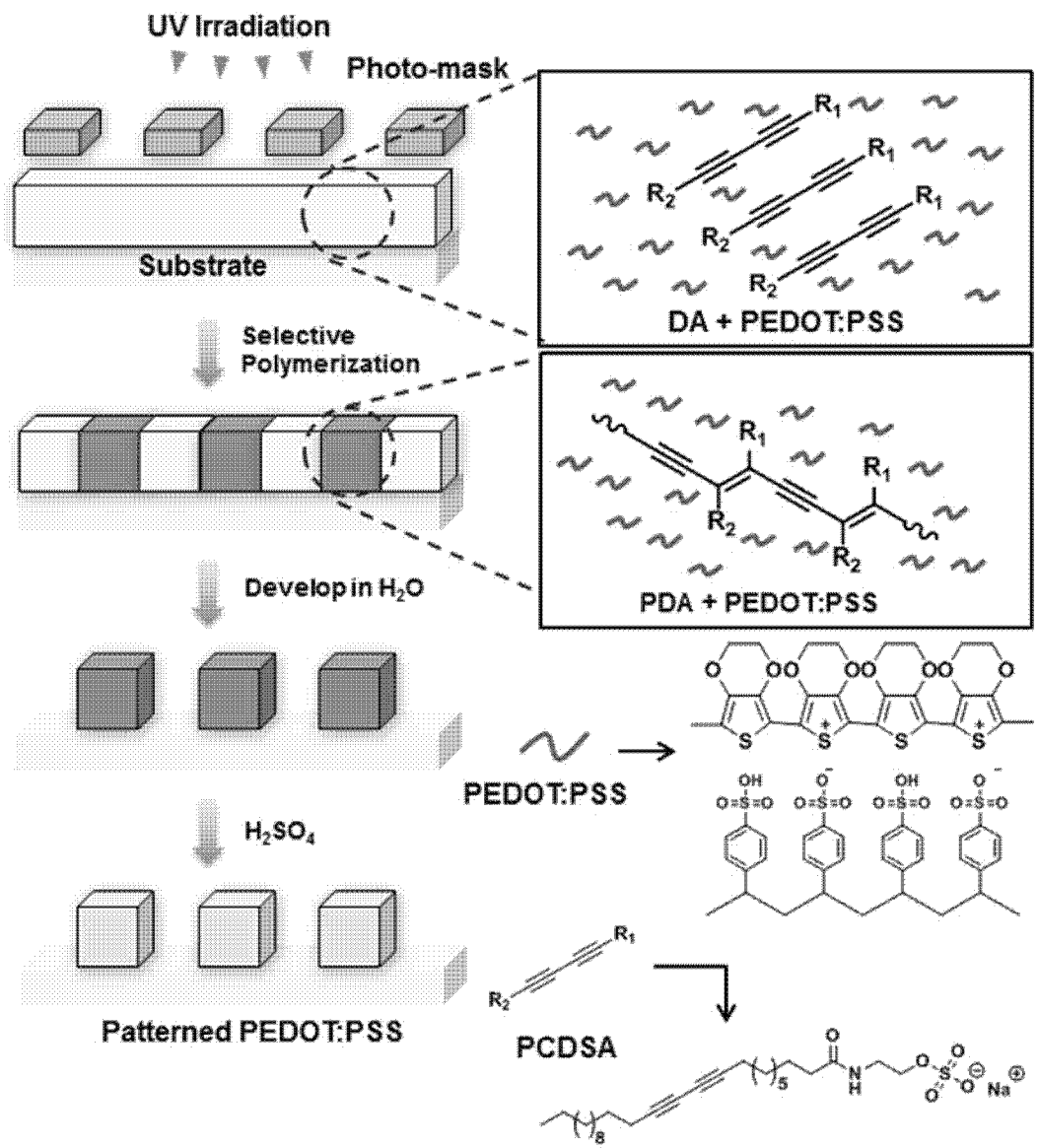

[FIG. 2A]
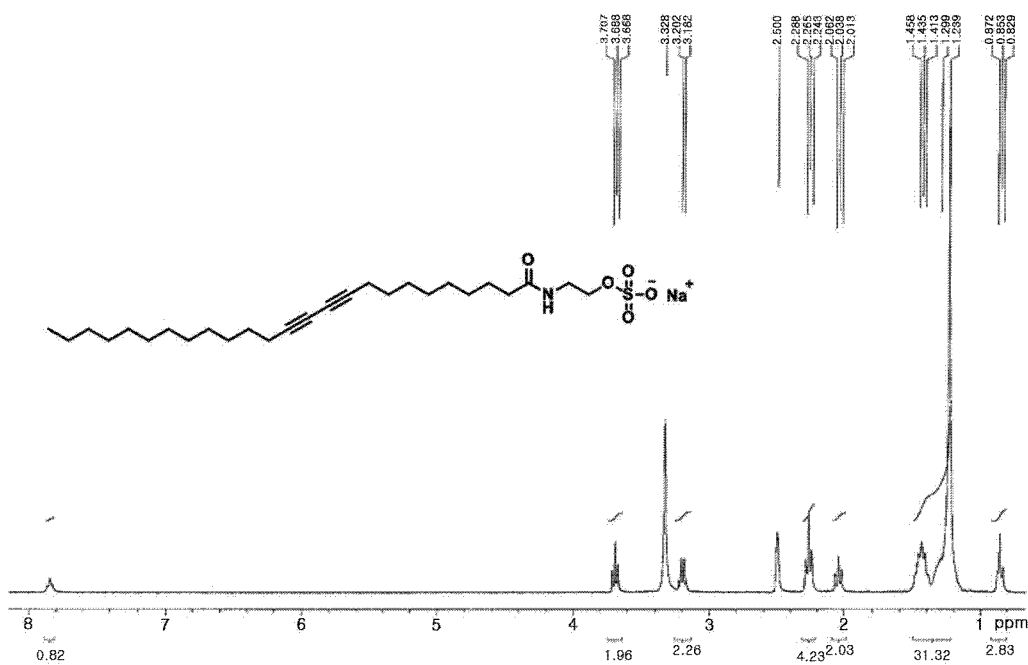
[FIG. 2B]
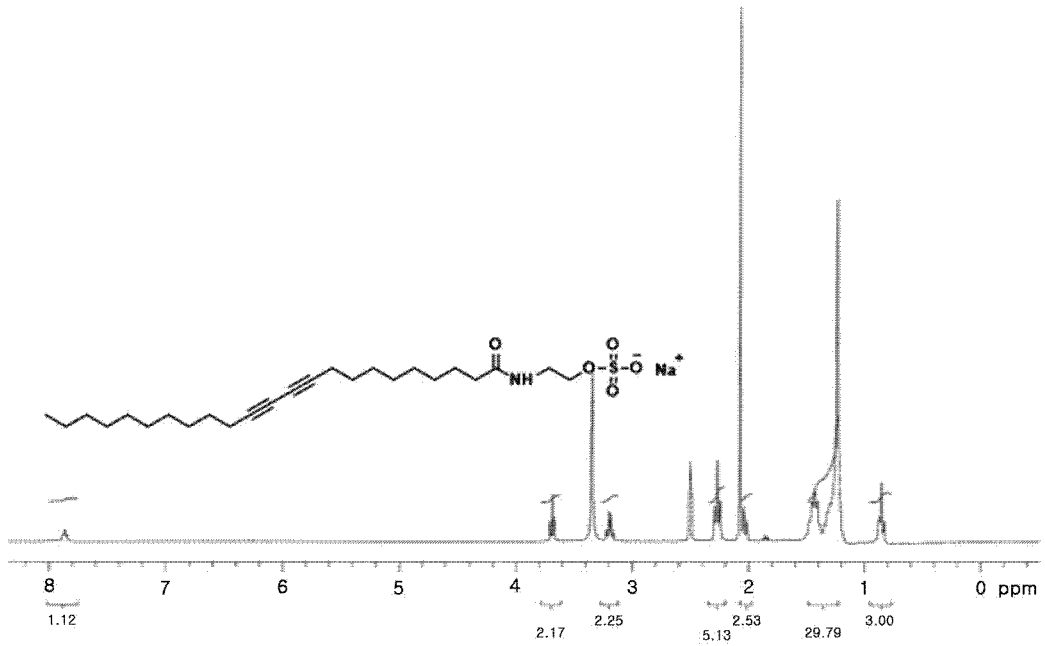

[FIG. 2C]
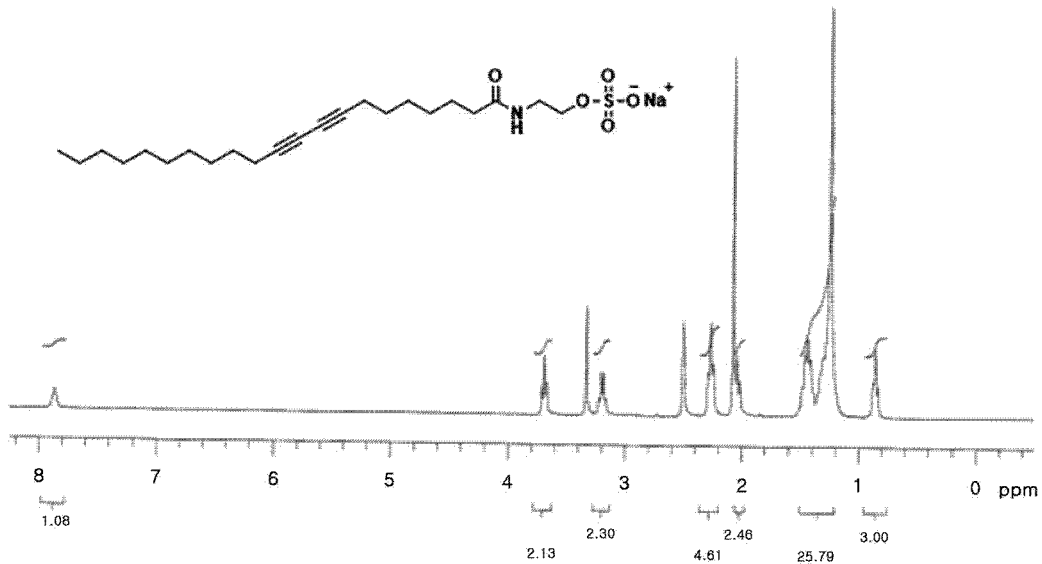
[FIG. 2D]
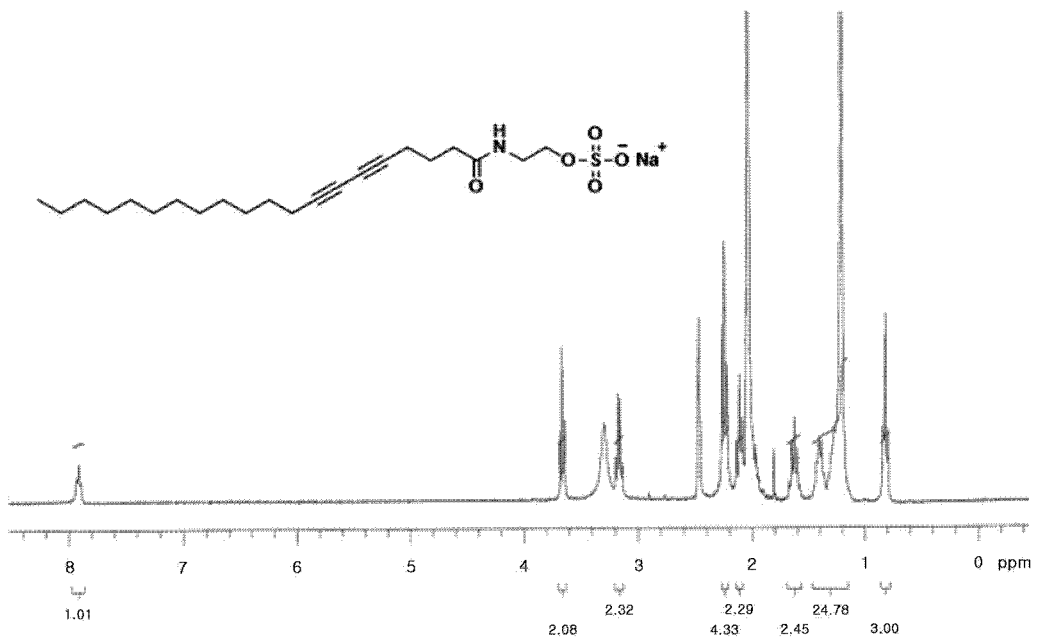

[FIG. 2E]
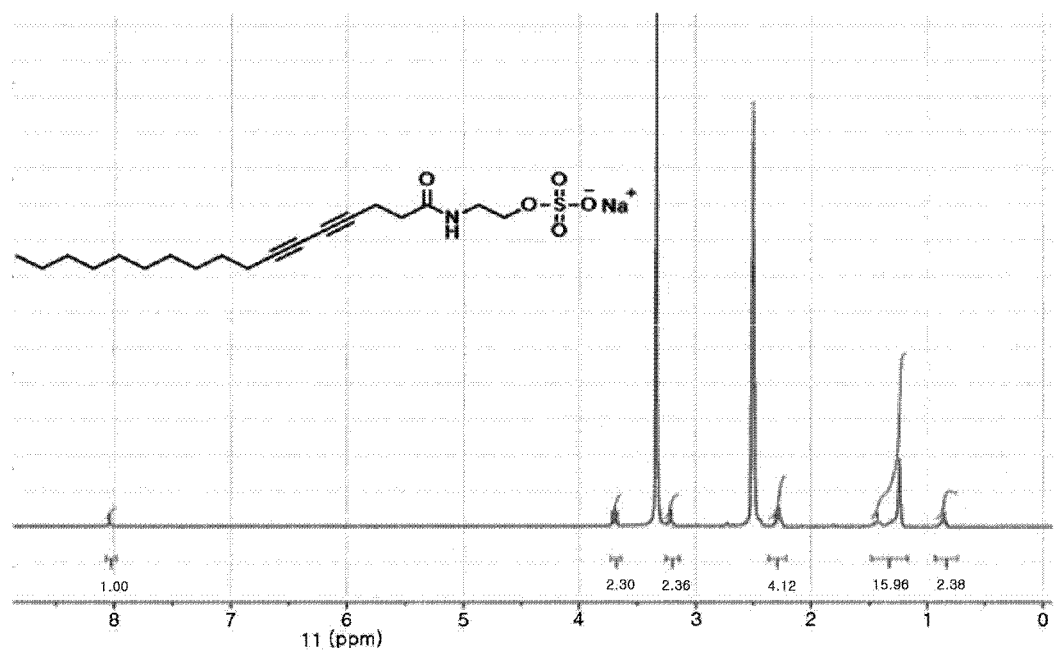
[FIG. 2F]
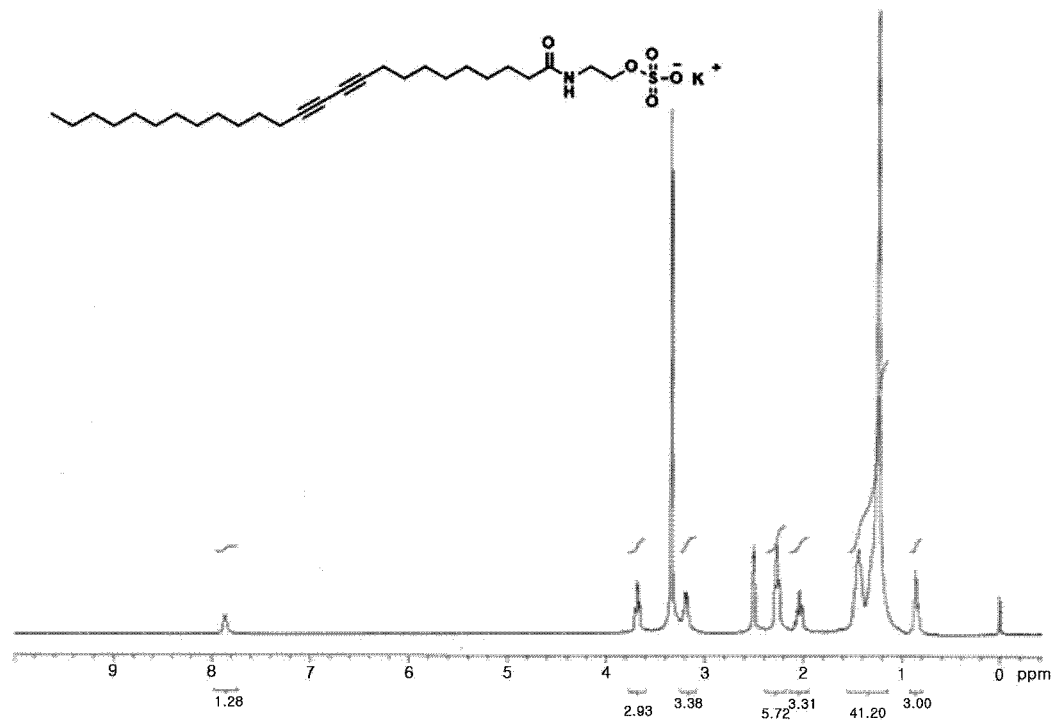

[FIG. 2G]
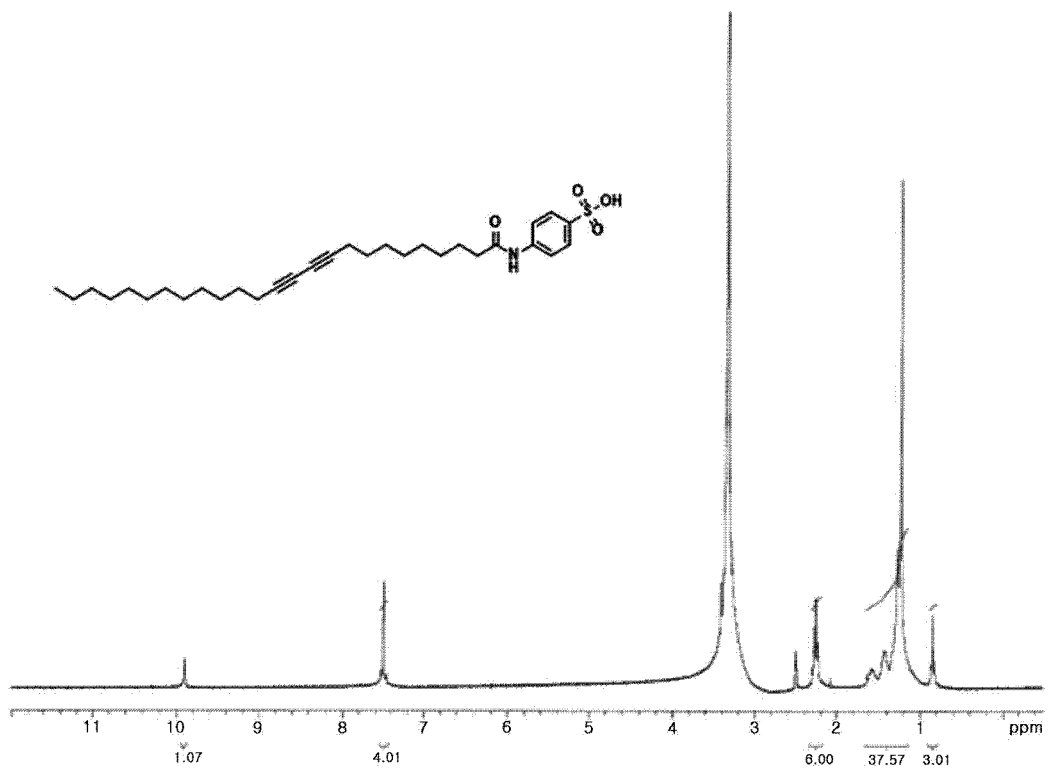

【FIG. 3】
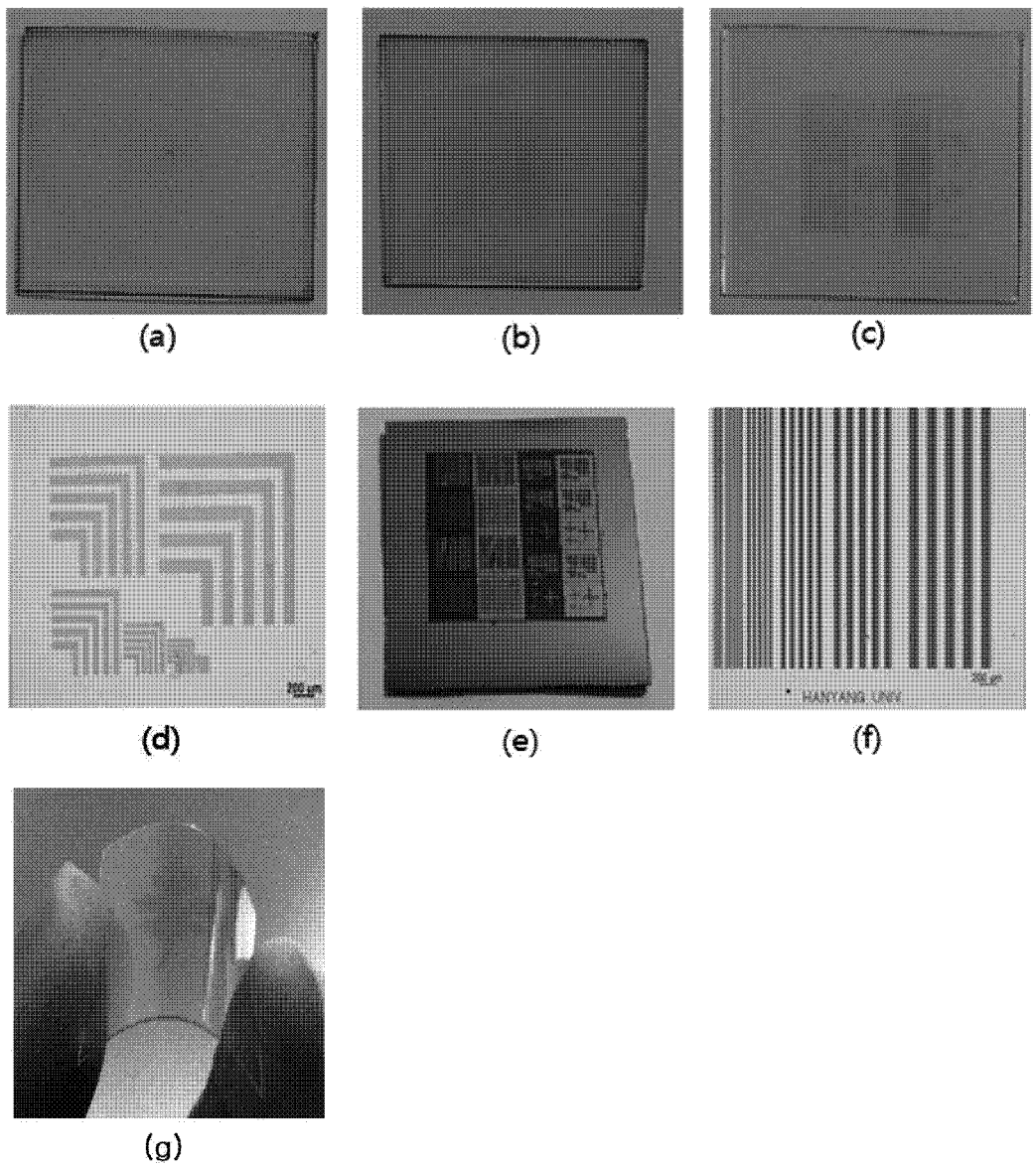

[FIG. 4]
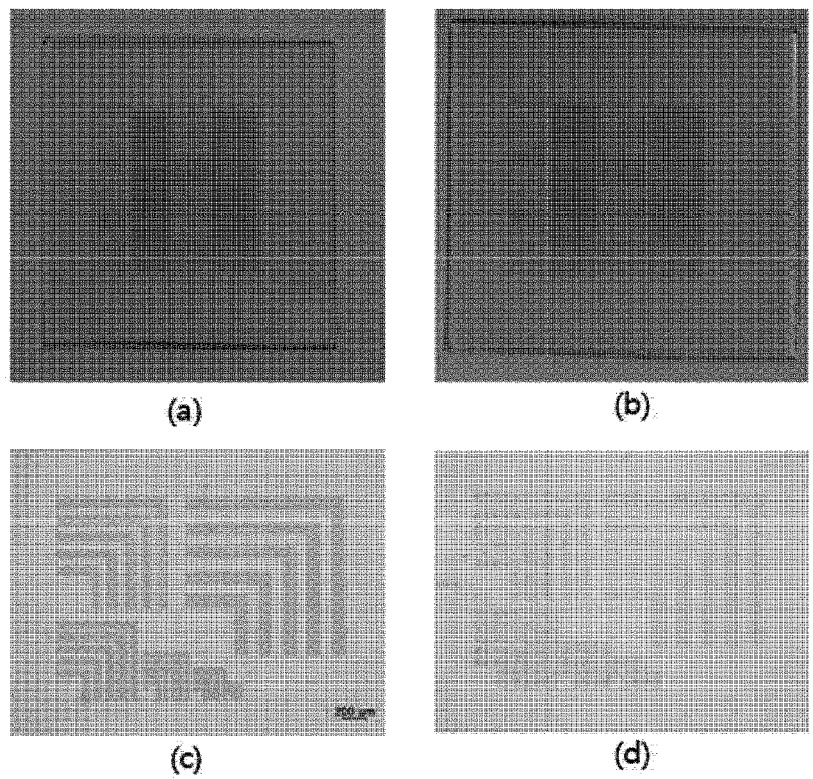
[FIG. 5]
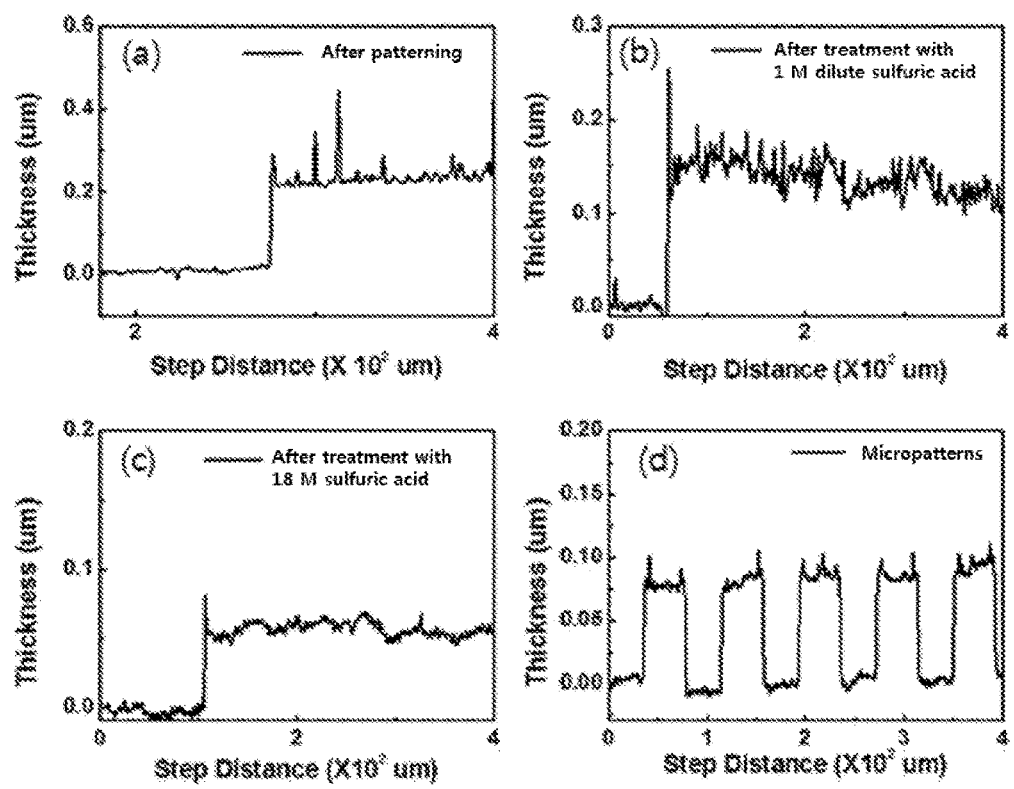

[FIG. 6]
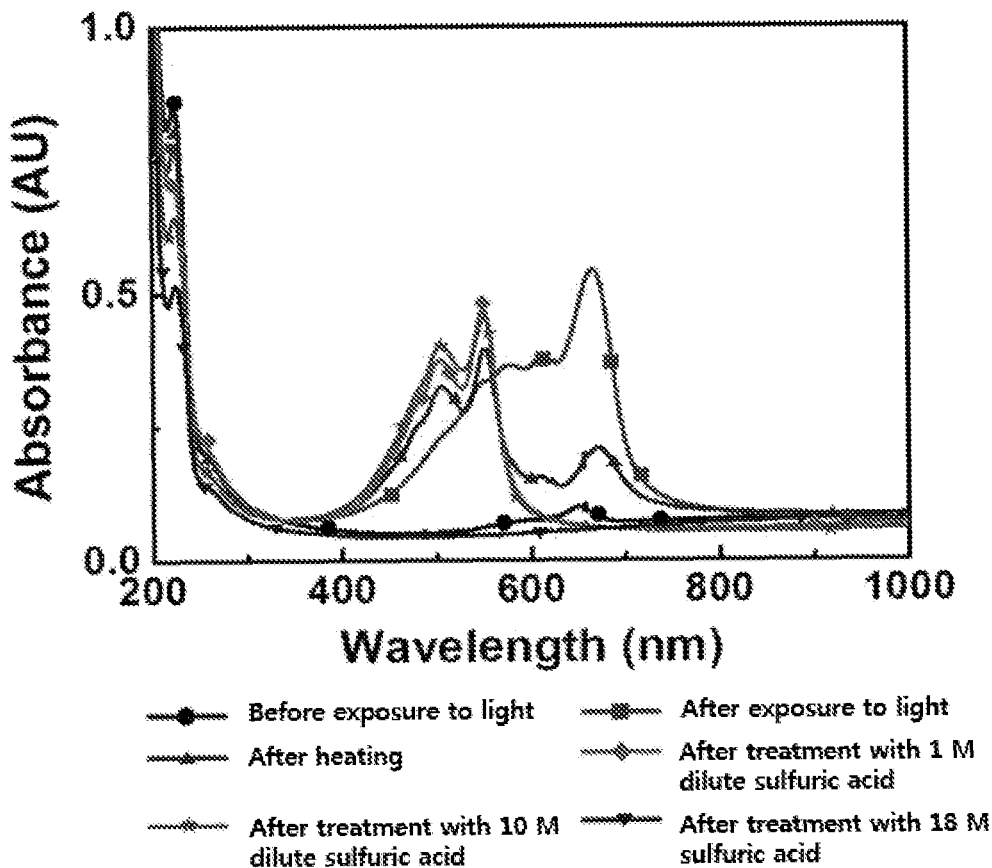
[FIG. 7]
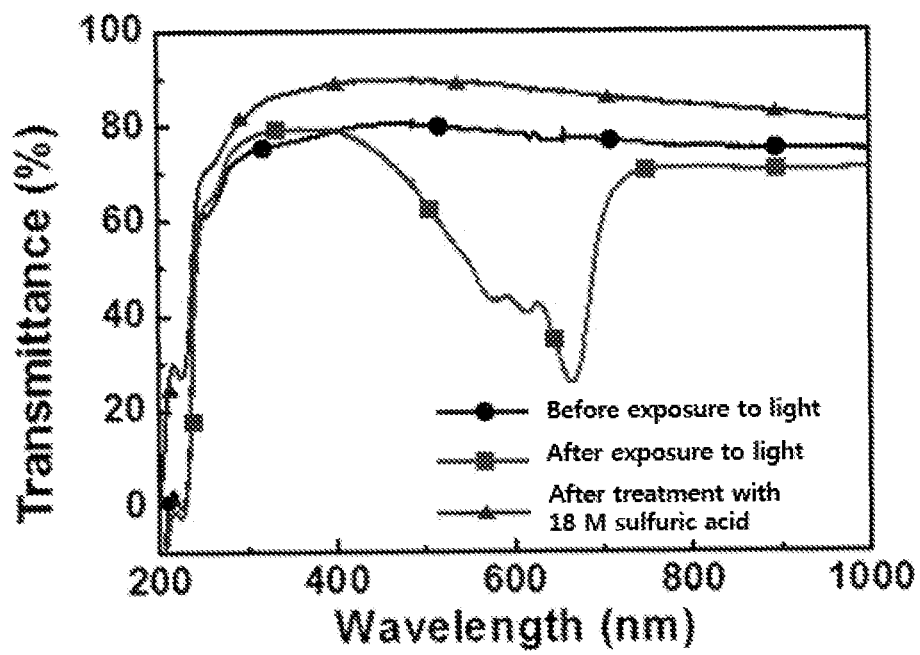

WATER-SOLUBLE DIACETYLENE, PHOTOLITHOGRAPHY COMPOSITION COMPRISING WATER-SOLUBLE DIACETYLENE MONOMER AND CONDUCTIVE POLYMER, AND FINE PATTERN PREPARATION METHOD USING SAME

CROSS REFERENCE TO RELATED APPLICATIONS

This application is a National Stage of International Application No. PCT/KR2017/004458 filed Apr. 26, 2017, claiming priority based on Korean Patent Application No. 10-2016-0054161, filed May 2, 2016.

TECHNICAL FIELD

Embodiments of the present invention relate to a method of forming patterns, and more particularly, to a method of forming conductive patterns.

BACKGROUND ART

In modern times, implementation of products that are light and thin and have maximized functionality may be the most important task in the advanced electronics industry. Therefore, printed circuit boards and electronic chips for future multifunctional high-speed information devices require much smaller linewidths.

Pixel electrodes of flat panel displays and flexible displays should be transparent and should satisfy electrical characteristics such as a sheet resistance of $10^3$ Ω/sq or less and a specific resistance of $10^{-3}$ Ωcm or less, and optical characteristics such as a transmittance of 80% or more in a visible light range of 380 to 780 nm. A transparent electrode can be applied to a PDP (Plasma Display Panel) optical filter and an electromagnetic shielding material for a sheet resistance range of ~100 Ω/sq, to an Organic Light Emitting Diode (OLED), a solar cell, and the like for a sheet resistance range of $10^0$ to $10^1$ Ω/sq, to a Liquid Crystal Display (LCD) and the like for a sheet resistance range of $10^2$ Ω/sq or less, and to a touchscreen, an EL keypad for mobile phones, and the like for a sheet resistance range of ~500 Ω/sq, depending upon conductivity thereof. Meanwhile, an electrode whose transmittance does not need to be taken into account can be used in applications such as a terminal electrode for Thin Film Transistors (TFT), an antenna for Radio Frequency Identification (RFID), and an antistatic film.

Recently, there is an increasing demand for LCDs and flat panel displays, which are thinner compared with conventional CRTs, particularly in large devices such as TVs and in small devices such as mobile phones and PDAs. Accordingly, demand for a transparent electrode used as a pixel electrode is also rapidly increasing, and besides indium tin oxide (ITO), organic materials such as a conductive polymer, a composite containing conductive powder, and a metal thin film have been researched and developed as new transparent electrode materials for flexible displays.

Conductive polymers can be broadly classified into a conductive composite material prepared by mixing a non-conductive general-purpose plastic matrix with a conductive filler such as metal or carbon, and an intrinsically conductive polymer (hereinafter referred to as ICP), a matrix of which is inherently conductive. In particular, in the case of ICP, various conductive polymers, such as polyparaphenylene, polypyrrole, polythiophene, and polyaniline, have been developed.

In particular, in implementing a flexible display, which is considered as a next generation display device, a conductive polymer patterning technology, which can realize a micrometer-scale wiring linewidth so as to construct a thin film transistor or a wiring electrode in the display device using a conductive polymer, has been extensively studied in academia and industry. With regard to such a conductive polymer patterning technique, a technique of electrochemically forming a film on a support and forming a desired pattern thereon using a photolithography process has been commonly used due to the intrinsic properties of a conductive polymer insoluble in an organic solvent. However, the process is disadvantageous in that it is complicated, takes a long time, uses respective photomasks for different patterns so as to implement various patterns, and generates large volumes of waste during the process.

Poly(3,4-ethylenedioxythiophene):poly(styrenesulfonate) (PEDOT:PSS), which is a type of conductive polymer, is one of the most widely used materials because it has higher conductivity over many other conductive plastic materials and good transparency in a visible light region, is soluble in water and thus allows for an eco-friendly solution preparation process, and has excellent stability. However, PEDOT:PSS has a very low conductivity of 1 S/cm and is insufficient for use as a transparent electrode. Accordingly, PEDOT:PSS should be coated with a thin film to increase transmittance, which causes an increase in surface resistance. Therefore, there are difficulties in applying PEDOT:PSS to actual transparent electrodes. Recently, as a conductive polymer patterning method, a solution process of printing a conductive polymer, PEDOT:PSS, dispersed in an aqueous solution on a support in a short time using an inkjet printer or a screen printing method was developed. However, inkjet and screen printing methods have limitations in increasing the resolution of patterns.

In addition, a recently published non-patent document, "Photolithographic Micropatterning of Conducting Polymers on Flexible Silk Matrices, *Advanced Materials* 2016, 28, 1406-1412," proposes a method of forming conductive micropatterns wherein an expensive silk protein that can be decomposed in response to light is mixed with a water-soluble PEDOT:PSS polymer and then conductive micropatterns are formed using a photolithography technology. However, this method results in very poor electrical conductivity such as a sheet resistance of 2.3085±0.6602 KΩ/sq.

Meanwhile, a recently published non-patent document, "Solution-Processed Metallic Conducting Polymer Films as Transparent Electrode of Optoelectronic Devices, *Advanced Materials* 2012, 24, 2436-2440," reported that a 1.0 M sulfuric acid solution was dropped onto a PEDOT:PSS thin film, whereby an electrical conductivity of 3,065 S/cm was exhibited. However, this document does not propose an optimal production method of increasing conductivity and is not related to a micropattern formation technology with an applied photolithography technology.

DISCLOSURE

Technical Problem

Accordingly, example embodiments of the present invention provide a novel water-soluble diacetylene monomer compound and a method of preparing the same. Example embodiments of the present invention also provide a composition for photolithography including the water-soluble diacetylene monomer and a conductive polymer PEDOT-PSS. Example embodiments of the present invention also provide a method of forming micropatterns using the composition for photolithography.

Technical Solution

Some embodiments provide a water-soluble diacetylene represented by Formula 1 below:

$CH_3-(CH_2)_n-C\equiv C-C\equiv C-(CH_2)_m-A-(CH_2)_x-B$  [Formula 1]

wherein n is 2 to 20, m is 2 to 15, x is 0 to 10, A is CONH, COO or CONH—Ar (when A is CONH—Ar, x=0, wherein Ar is a phenyl group or a naphthalene group), and B is $OSO_3B'$ or $OPO_3B'$, wherein B' is H, Li, Na, K, Rb or Cs.

Other embodiments provide a method of preparing a water-soluble diacetylene represented by Formula 1-1 below. First, a solution is obtained by dissolving diacetylenic acid and aminoalkyl hydrogen sulfate, aminoalkyl hydrogen phosphate, hydroxyalkyl hydrogen sulfate, or hydroxyalkyl hydrogen phosphate in an organic solvent. An alkanephosphonic anhydride is added to and reacted with the solution, thereby obtaining a water-soluble diacetylene represented by Formula 1-1 below:

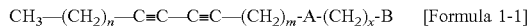
$CH_3-(CH_2)_n-C\equiv C-C\equiv C-(CH_2)_m-A-(CH_2)_x-B$  [Formula 1-1]

wherein n is 2 to 20, m is 2 to 15, x is 2 to 10, A is CONH or COO, and B is $OSO_3H$ or $OPO_3H$.

Still other embodiments provide a composition for photolithography. The composition for photolithography includes a water-soluble conductive polymer and the water-soluble diacetylene monomer represented by Formula 1.

Yet other embodiments provide a method of forming fine patterns. First, a composition for photolithography including a water-soluble conductive polymer and the water-soluble diacetylene monomer represented by Formula 1 is provided. The composition for photolithography applied as a coating on a substrate, thereby forming a conductive polymer-containing thin film. A light exposure step which includes disposing a photomask on the conductive polymer-containing thin film and irradiating the photomask with ultraviolet light to form a first region, which includes polydiacetylene formed by crosslinking of the diacetylene monomer along with the conductive polymer, and a second region, in which the diacetylene monomer remains due to the photomask blocking ultraviolet light, is performed. The second region is selectively removed, thereby forming conductive polymer micropatterns.

Advantageous Effects

In accordance with the present invention, a novel water-soluble diacetylene monomer which does not aggregate even when mixed with a water-soluble conductive polymer is provided. Accordingly, a uniform composition for photolithography can be prepared by mixing a water-soluble conductive polymer with the diacetylene monomer, and fine patterns can be formed using the composition. More particularly, when a thin film is manufactured using the composition and then is irradiated with light, only light-irradiated portions of a diacetylene monomer are selectively crosslinked due to photopolymerization, thereby obtaining insoluble negative-type micropatterns.

In particular, the novel water-soluble diacetylene monomer according to the present invention is an amphipathic substance, in molecules of which both hydrophilic and hydrophobic functional groups are present, and can form a complex along with a water-soluble conductive polymer to have a spontaneously oriented layer structure. That is, in the spontaneously oriented layer structure, main chains of the water-soluble conductive polymer are extended along with the novel water-soluble diacetylene monomer, whereby electrons can easily flow through main chains of the conjugated polymer.

In addition, the present invention includes a step of doping with a dopant such as sulfuric acid, thereby greatly improving electrical conductivity. Since polydiacetylene is basically an insulator, electrical conductivity can be greatly increased if it can be removed from a micro-patterned thin film. Meanwhile, polydiacetylene functional groups can be removed by a highly-acidic dopant such as sulfuric acid. Accordingly, polydiacetylene can be removed from a thin film by adding a step of doping with a dopant such as sulfuric acid, thereby greatly increasing electrical conductivity. In addition, in accordance with the present invention, a thin film and micropatterns can be formed on flexible PET plastics as well as silicon wafers and glass. Therefore, the present invention can be applied to various organic electronic devices such as solar cells and super capacitors.

DESCRIPTION OF DRAWINGS

FIG. 1 is a schematic diagram illustrating a method of forming micropatterns according to an embodiment of the present invention.

FIG. 2A is a $^1H$ NMR graph of sodium 2-pentacosa-10,12-diynamidoethyl sulfate (PCDSA-Na) synthesized by Synthesis Example 1.

FIG. 2B is a $^1H$ NMR graph of sodium 2-tricosa-10,12-diynamidoethyl sulfate (TCDSA-Na) synthesized by Synthesis Example 2.

FIG. 2C is a $^1H$ NMR graph of sodium 2-heneicosa-8,10-diynamidoethyl sulfate (HCDSA-Na) synthesized by Synthesis Example 3.

FIG. 2D is a $^1H$ NMR graph of sodium 2-eicosa-5,7-diynamidoethyl sulfate (ECDSA-Na) synthesized by Synthesis Example 4.

FIG. 2E is a $^1H$ NMR graph of sodium 2-heptadeca-4,6-diynamidoethyl sulfate (HDDSA-Na) synthesized by Synthesis Example 5.

FIG. 2F is a $^1H$ NMR graph of potassium 2-pentacosa-10,12-diynamidoethyl sulfate (PCDSA-K) synthesized by Synthesis Example 6.

FIG. 2G illustrates a 1H NMR graph of 4-(pentacosa-10,12-diynamido)benzenesulfonic acid (PCDSFA) synthesized by Synthesis Example 8.

FIG. 3 is photographs of (a) a thin film formed after spin-coating application of the PCDSA-PEDOT:PSS solution obtained during the process of Manufacturing Example 1 on a glass substrate, (b) the thin film after exposure to light, (c) entire patterns developed on a glass substrate, (d) micropatterns developed on the glass substrate (an enlarged view of (c), scale bar: 200 μm)), (e) entire patterns developed on a silicon wafer, (f) micropatterns developed on the silicon wafer (an enlarged view of (e), scale bar: 200 μm), and (g) entire patterns developed on a PET substrate.

FIG. 4 is photographs of (a) entire patterns treated with dilute sulfuric acid (1 M), (b) entire patterns treated with concentrated sulfuric acid (18 M), (c) micropatterns treated with dilute sulfuric acid (1 M) (an enlarged view of (a), scale bar: 200 μm), and (d) micropatterns treated with concentrated sulfuric acid (18 M) (an enlarged view of (c), scale bar: 200 μm), wherein the patterns were obtained according to Manufacturing Example 3.

FIG. 5 is graphs illustrating the thicknesses of (a) patterns before addition of a sulfuric acid solution, (b) patterns after addition of a 1 M dilute sulfuric acid, and (c, d) patterns after addition of 18 M concentrated sulfuric acid, wherein the patterns were obtained during the process of Manufacturing Example 3.

FIG. 6 illustrates UV-vis absorption spectra of samples obtained during the process of Manufacturing Examples 1 and 3.

FIG. 7 illustrates transmittance of samples obtained during the process of Manufacturing Examples 1 and 3.

MODES OF THE INVENTION

Exemplary embodiments of the present invention will now be described in detail. Objectives, features and advantages of the present invention will be more easily understood through the embodiments. This invention may, however, be embodied in many different forms and should not be construed as limited to the embodiments set forth herein. Rather, these embodiments are provided so that this invention will fully convey the scope of the invention to those of ordinary skill in the art. Therefore, the scope of the present invention is not limited to the following embodiments.

Water-Soluble Diacetylene

A water-soluble diacetylene according to an embodiment of the present invention may be represented by Formula 1 below:

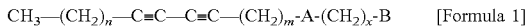
[Formula 1]

wherein n may be 2 to 20, m may be 2 to 15, and x may be 0 to 10. For example, n may be 2 to 13, m may be 2 to 8, and x may be 2 to 5. A may be C(O)NH, C(O)O, or CONH—Ar. When A is CONH—Ar, x=0. Here, Ar may be a phenyl group or a naphthalene group. B is $OSO_3B'$ or $OPO_3B'$. Here, B' may be H, Li, Na, K, Rb or Cs.

Since diacetylene includes sulfonic groups, phosphate groups, and the like, which have a high ionization degree, at chain terminals thereof, it can be hydrophilic despite inclusion of long alkyl chains which are hydrophobic functional groups. When diacetylene includes a sulfonate ($OSO_3H$) or phosphate ($OPO_3H$) group having an alkali metal instead of a hydrogen ion ($H^+$), i.e., an alkali metal sulfonate or an alkali metal phosphate, hydrophilicity may be further increased. Meanwhile, A in the middle of the chain may be CONH (amide), COO (ester) or CONH—Ar (wherein x=0).

When such a water-soluble diacetylene is mixed with a water-soluble conductive polymer, it reduces a risk of aggregation. Accordingly, the resultant mixture may be advantageously used to manufacture a thin film for photolithography. In particular, since known diacetylenic acids or salts thereof include carboxyl groups (COOH) or metal salts of carboxylic acids at terminals thereof, an aggregation phenomenon occurs when the known diacetylenic acid or the salts are mixed with a water-soluble conductive polymer. Accordingly, the known diacetylenic acids or salts might not be suitable for a composition for photolithography. Meanwhile, when the number (n, m, and x) of carbon chains in the diacetylene is within the defined range, appropriate water solubility may be exhibited.

The water-soluble conductive polymer may be poly(3,4-ethylenedioxythiophene) (PEDOT):poly(styrenesulfonate) (PSS).

The compound represented by Formula 1 may be a water-soluble diacetylene represented by Formula 2 below:

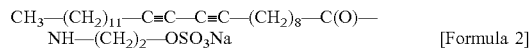
[Formula 2]

The water-soluble diacetylene may be obtained by dissolving diacetylenic acid and aminoalkyl hydrogen sulfate, aminoalkyl hydrogen phosphate, hydroxyalkyl hydrogen sulfate, or hydroxyalkyl hydrogen phosphate in an organic solvent, followed by adding an alkanephosphonic anhydride thereto and reacting therewith.

Here, the water-soluble diacetylene may be represented by Formula 1-1 below:

[Formula 1-1]

wherein n is 2 to 20, m is 2 to 15, x is 2 to 10, A is CONH or COO, and B is $OSO_3H$ or $OPO_3H$.

The water-soluble diacetylene represented by Formula 1-1 may be represented by Formula 1-1a below:

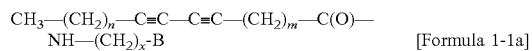
[Formula 1-1a]

The diacetylenic acid may include one or more selected from the group consisting of PCDA (10,12-pentacosadiynoic acid), TCDA (10,12-tricosadiynoic acid), ECDA (5,7-eicosadiynoic acid), HCDA (8,10-heneicosadiynoic acid) and HDDA (4,6-heptadecadiynoic acid).

The aminoalkyl hydrogen sulfate may be 2-aminoethyl hydrogen sulfate, the hydroxyalkyl hydrogen sulfate may be 2-hydroxyethyl hydrogen sulfate, the aminoalkyl hydrogen phosphate may be 2-aminoethyl dihydrogen phosphate, and the hydroxyalkyl hydrogen phosphate may be 2-hydroxyethyl hydrogen phosphate.

The organic solvent may include one or more selected from the group consisting of N,N-dimethylformamide, dimethylsulfoxide (DMSO), chloroform and dichloromethane. In addition, the alkanephosphonic anhydride may be 1-propanephosphonic anhydride. The step of adding an alkanephosphonic anhydride and allowing reaction to occur may be performed by stirring at 1 to 35° C. for 12 to 24 hours.

In addition, the diacetylene represented by Formula 1-1 is treated with an alkali metal compound, thereby obtaining a water-soluble diacetylene represented by Formula 1-2 below:

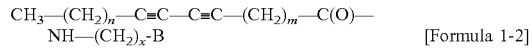
[Formula 1-2]

wherein n is 2 to 20, m is 2 to 15, x is 2 to 10, and B is $OSO_3B'$ or $OPO_3B'$, wherein B' is Li, Na, K, Rb or Cs.

In this step, hydrogen ions ($H^+$) of sulfonate groups ($OSO_3H$) and phosphate groups ($OPO_3H$) at terminals of the diacetylene represented by Formula 1-1 are substituted with alkali metals such as Li, Na, K, Rb or Cs, whereby the diacetylene includes an alkali metal sulfonate or an alkali metal phosphate. Accordingly, hydrophilicity may be further increased.

The alkali metal compound may be sodium bicarbonate. For another example, the alkali metal compound may be NaOH, LiOH, KOH, RbOH, or CsOH. In this case, a diacetylene monomer in a conjugate base form may be produced.

Conductive Polymer Composition for Photolithography

A conductive polymer composition for photolithography according to an embodiment of the present invention includes a water-soluble conductive polymer and a water-soluble diacetylene monomer represented by any one of Formulas 1, 2, 1-1, and 1-2. The water-soluble conductive polymer may be poly(3,4-ethylenedioxythiophene) (PEDOT):poly(styrenesulfonate) (PSS).

The composition may include water as a solvent. The composition may include 0.01 to 50 parts by weight, particularly 0.5 to 5 parts by weight, for example 2 parts by weight, of a water-soluble diacetylene monomer based on 100 parts by weight of a water-soluble conductive polymer. Meanwhile, water may be included in an amount of 10,000 to 50,000 parts by weight based on 100 parts by weight of a water-soluble conductive polymer.

A conductive polymer composition having the composition ratio may have a viscosity suitable for forming a coating on a substrate.

The conductive polymer composition for photolithography may be obtained by dissolving the water-soluble diacetylene monomer in an aqueous conductive polymer solution and may be present in a solution state without aggregation. To accomplish this, an aqueous conductive polymer solution may be mixed with a water-soluble diacetylene monomer, and then sonication may be additionally performed, thereby obtaining a uniform solution.

Method of Forming Micropatterns Using Conductive Polymer Composition for Photolithography FIG. 1 is a schematic diagram illustrating a method of forming micropatterns according to an embodiment of the present invention.

Referring to FIG. 1, a conductive polymer-containing thin film may be formed by applying the conductive polymer composition for photolithography, i.e., a composition including a water-soluble conductive polymer and a water-soluble diacetylene monomer represented by any one of Formulas 1, 2, 1-1, and 1-2, as a coating on a substrate.

The substrate may also be referred to as a base or a support, and may be a silicon wafer, a glass substrate, a plastic substrate, a paper, a support coated with another thin film, or a metal substrate. A step of forming the conductive polymer-containing thin film may be performed using, without being limited to, a spin coating method, a doctor blade method, etc. For example, the conductive polymer-containing thin film may be formed by spin-coating, and a thin film having an appropriate thickness may be obtained by carrying out a minimum number of coating process.

Subsequently, a photomask is disposed on the conductive polymer-containing thin film and the photomask is irradiated with ultraviolet light, thereby forming conductive polymer micropatterns on the substrate. The step of forming micropatterns may include a light exposure step of forming the first region, which includes the polydiacetylene formed by crosslinking of the diacetylene monomer due to irradiation with ultraviolet light along with the conductive polymer, and the second region, in which a diacetylene monomer remains due to the photomask blocking ultraviolet light, and a development step of selectively washing off the second region.

The light exposure step may be performed by irradiating ultraviolet light of 220 to 330 nm for 10 to 20 minutes. Polydiacetylene formed by crosslinking the diacetylene monomer in a specific region with ultraviolet light is insoluble in water, and may appear blue due to having a π-conjugated main chain as a result of superposition of π-orbital. Meanwhile, since the second region, in which a diacetylene monomer remains due to the photomask blocking the ultraviolet light, maintains the water solubility thereof, it may be washed off with an aqueous solution, e.g., water. As a result, negative-type micropatterns may be formed. In addition, the micropatterns may have a nanoscale or microscale linewidth.

The conductive polymer in the micropatterns may be doped by applying a dopant on the micropatterns. The dopant may include one or more selected from the group consisting of sulfuric acid, sulfonic acid, formic acid, hydrochloric acid, perchloric acid, nitric acid, acetic acid, dimethylformamide (DMF), dimethyl sulfoxide (DMSO), and ethylene glycol. The sulfonic acid may be selected from the group consisting of methanesulfonic acid, trifluoromethanesulfonic acid, perchloric acid, benzenesulfonic acid, and para-toluenesulfonic acid, but the present invention is not limited thereto. The electrical conductivity of the conductive polymer may be increased by doping with a dopant.

The doping step may include a step of treating the micropatterns with a solution including a dopant, a step of washing the same with a solvent such as ethanol, and a step of drying the washed thin film. Here, the drying may be performed at 60 to 160° C. The step of treating the micropatterns with a solution including a dopant may be performed using a method of spraying, spreading, or adding the solution including a dopant on the micropatterns or a method of immersing the substrate, on which the micropatterns have been formed, in the solution including a dopant.

The dopant may be an aqueous solution of a strong acid, particularly a concentrated aqueous solution of a strong acid. For example, the dopant may be hydrochloric acid, nitric acid, or sulfuric acid with a molar concentration of 15 M or more. When such an aqueous solution of a strong acid is applied on the micropatterns, the polydiacetylene in the micropatterns may be decomposed. In addition, when the conductive polymer is PEDOT:PSS, PSS may also be etched. As a result, only the conductive polymer remains in the micropatterns treated with the aqueous solution of a strong acid, whereby conductivity may be greatly increased.

Meanwhile, the water-soluble diacetylene monomer represented by Formula 1 has an amphiphilic molecular structure by including a hydrophobic alkyl chain, hydrophilic terminals, which are sulfonate groups or phosphate groups, and an amide (CONH) or ester (COO) bond. Such a diacetylene monomer may be spontaneously oriented when mixed with the conductive polymer because it interacts with the conductive polymer through a hydrogen bond, etc. Accordingly, when the composition of the present invention is applied and then photopolymerization is performed, the conductive polymer is also spontaneously oriented due to spontaneous orientation of the polydiacetylene in the micropatterns, whereby the electrical conductivity of the micropatterns may be increased. In addition, as described above, the conductivity of the conductive polymer may be further increased by the doping with a dopant. Further, when a concentrated strong acid is used as a dopant, the polydiacetylene may be decomposed and removed from the micropatterns, whereby the conductivity of the micropatterns may be further increased. Even when the polydiacetylene is removed, the orientation of the conductive polymer may be maintained.

Meanwhile, the micropatterns may be used as electrodes for a display device, an electrochemical device, or the like, particularly for an organic electronic device. The display device may be an organic light emitting diode, and the electrochemical device may be an organic solar cell or a dye-sensitized solar cell. Examples of other organic electronic devices include organic thin film transistors.

Now, the present invention will be described in more detail with reference to the following preferred experimental examples. However, these experimental examples are provided for illustrative purposes only, and the scope of the present invention is not limited to the experimental examples.

Synthesis Example: Diacetylene Monomer Synthesis

Synthesis Example 1: Synthesis of sodium 2-pentacosa-10,12-diynamidoethyl sulfate (PCDSA-Na)

10,12-pentacosadiynoic acid (PCDA, 1.0 g, 2.67 mmol) and 2-aminoethyl hydrogen sulfate (0.31 g, 2.22 mmol) were dissolved in N,N-dimethylformamide (20 mL), and then triethylamine (0.67 g, 6.66 mmol) and a 50% solution of 1-1-propanephosphonic anhydride (2.12 mL, 3.33 mmol) in an ethyl acetate solvent were added thereto, followed by a reaction while stirring with a magnetic stirrer at room temperature for 18 hours. After the reaction, extraction was performed with water and dichloromethane, and then a diacetylene monomer, PCDSA-Na, was synthesized by treating with sodium bicarbonate.

IR: (cm$^{-1}$) vmax 723, 781, 955, 1024, 1079, 1221, 1460, 1557, 1641, 2918, 2952, 3295. $^1$H NMR: (300 MHz, DMSO-d$_6$): δ 7.85 (t, 1H) 3.69 (t, J=5.7 Hz, 2H), 3.19 (q, J=5.7 Hz, 2H), 2.26 (t, J=6.9 Hz, 4H), 2.04 (t, J=7.2 Hz, 2H), 1.46-1.23 (m, 32H), 0.85 (t, J=5.7 Hz, 3H). $^{13}$C NMR: (75 MHz, DMSO-d$_6$): δ 172.14, 77.96, 65.35, 65.31, 64.38, 35.30, 31.30, 29.00, 28.94, 28.86, 28.70, 28.38, 28.23, 28.16, 27.74, 27.68, 25.20, 22.10, 18.27, 13.96.

FIG. 2A is a $^1$H NMR graph of sodium 2-pentacosa-10,12-diynamidoethyl sulfate (PCDSA-Na) synthesized by Synthesis Example 1.

Synthesis Example 2: Synthesis of sodium 2-tricosa-10,12-diynamidoethyl sulfate (TCDSA-Na)

A diacetylene monomer, TCDSA-Na, was synthesized in the same manner as in Synthesis Example 1, except that 2.67 mmol of 10,12-tricosadiynoic acid (TCDA) was used instead of 10,12-pentacosadiynoic acid (PCDA, 1.0 g, 2.67 mmol).

FIG. 2B is a $^1$H NMR graph of sodium 2-tricosa-10,12-diynamidoethyl sulfate (TCDSA-Na) synthesized by Synthesis Example 2.

Synthesis Example 3: Synthesis of sodium 2-heneicosa-8,10-diynamidoethyl sulfate (HCDSA-Na)

A diacetylene monomer, HCDSA-Na, was synthesized in the same manner as in Synthesis Example 1, except that 2.67 mmol of 8,10-heneicosadiynoic acid (HCDA) was used instead of 10,12-pentacosadiynoic acid (PCDA, 1.0 g, 2.67 mmol).

FIG. 2C is a $^1$H NMR graph of sodium 2-heneicosa-8,10-diynamidoethyl sulfate (HCDSA-Na) synthesized by Synthesis Example 3.

Synthesis Example 4: Synthesis of sodium 2-eicosa-5,7-diynamidoethyl sulfate (ECDSA-Na)

A diacetylene monomer, ECDSA-Na, was synthesized in the same manner as in Synthesis Example 1, except that 2.67 mmol of 5,7-eicosadiynoic acid (ECDA) was used instead of 10,12-pentacosadiynoic acid (PCDA, 1.0 g, 2.67 mmol).

FIG. 2D is a $^1$H NMR graph of sodium 2-eicosa-5,7-diynamidoethyl sulfate (ECDSA-Na) synthesized by Synthesis Example 4.

Synthesis Example 5: Synthesis of sodium 2-heptadeca-4,6-diynamidoethyl sulfate (HDDSA-Na)

A diacetylene monomer, HDDSA-Na, was synthesized in the same manner as in Synthesis Example 1, except that 2.67 mmol of 4,6-heptadecadiynoic acid (HDDA) was used instead of 10,12-pentacosadiynoic acid (PCDA, 1.0 g, 2.67 mmol).

FIG. 2E is a $^1$H NMR graph of sodium 2-heptadeca-4,6-diynamidoethyl sulfate (HDDSA-Na) synthesized by Synthesis Example 5.

Synthesis Example 6: Synthesis of potassium 2-pentacosa-10,12-diynamidoethyl sulfate (PCDSA-K)

10,12-pentacosadiynoic acid (PCDA, 1.0 g, 2.67 mmol) and 2-aminoethyl hydrogen sulfate (0.31 g, 2.22 mmol) were dissolved in N,N-dimethylformamide (20 mL), and then triethylamine (0.67 g, 6.66 mmol) and a 50% solution of 1-propanephosphonic anhydride (2.12 mL, 3.33 mmol) in an ethyl acetate solvent were added thereto, followed by a reaction while stirring with a magnetic stirrer at room temperature for 18 hours. After the reaction, extraction was performed using water and dichloromethane, and then a diacetylene monomer, PCDSA-K, was synthesized by treating with potassium hydroxide.

FIG. 2F is a $^1$H NMR graph of potassium 2-pentacosa-10,12-diynamidoethyl sulfate (PCDSA-K) synthesized by Synthesis Example 6.

Synthesis Example 7: Synthesis of sodium 2-(pentacosa-10,12-diynoloxy)ethane-1-sulfinate (PCDOSA-Na)

10,12-pentacosadiynoic acid (PCDA, 1.0 g, 2.67 mmol) was dissolved in dichloromethane (20 ml), and then N,N'-dicyclohexylcarbodiimide (DCC, 0.66 mg) and 4-dimethylaminopyridine (DMAP, 0.06 mg) were added thereto. A 2-hydroxy ethanesulfonic acid sodium salt (0.328 g, 2.22 mmol) was additionally added to and reacted with the mixture, followed by a reaction while stirring with a magnetic stirrer at room temperature for 18 hours. As a result, a diacetylene monomer, PCDOSA-Na, was synthesized.

Synthesis Example 8: Synthesis of 4-(pentacosa-10,12-diynamido)benzenesulfonic acid (PCDSFA)

10,12-pentacosadiynoic acid (PCDA, 1.0 g, 2.67 mmol) was prepared into PCDA-Cl using oxalyl chloride (0.40 ml, 8.01 mmol). PCDA-Cl and a sulfanilic salt were dissolved in N,N-dimethylformamide (20 mL), then triethylamine (3.345 ml, 24.03 mmol) was added thereto, followed by a reaction for 18 hours while stirring with a magnetic stirrer. After the reaction, a powder-type product was obtained through filtration with a filter. The obtained product was washed with ether, tetrahydrofuran, and DI water, thereby obtaining a diacetylene monomer, PCDSFA.

FIG. 2G illustrates a ¹H NMR graph of 4-(pentacosa-10,12-diynamido)benzenesulfonic acid (PCDSFA) synthesized by Synthesis Example 8.

Manufacturing Example 1: Preparation of Composition for Photolithography and Formation of Patterns 100 mg of the sodium 2-pentacosa-10,12-diynamidoethyl sulfate (PCDSA-Na) obtained in Synthesis Example 1 was dissolved in 10 ml of an aqueous PEDOT:PSS solution (manufactured by Sigma-Aldrich Co.), followed by sonication for 10 minutes such that sufficient dissolution was achieved. Filtration was performed with a 0.45 mm filter to remove impurities, thereby obtaining a PCDSA-PEDOT:PSS solution wherein the PCDSA monomer was dissolved in the aqueous PEDOT:PSS solution. The prepared solution was applied by spin-coating on a glass substrate to form a uniform thin film. A photomask was placed on the thin film and was irradiated with ultraviolet light with a strong wavelength of 254 nm for about 10 minutes, thereby forming light-exposed patterns in the film. Subsequently, the substrate, on which the light-exposed patterns had been formed, was carefully immersed in water so that parts except for the patterns was etched, thereby developing the patterns.

Manufacturing Example 2: Pattern Formation

Patterns were formed in the same manner as in Manufacturing Example 1, except that a silicon wafer was used instead of a glass substrate.

FIG. 3 is photographs of (a) a thin film formed after spin-coating application of the PCDSA-PEDOT:PSS solution obtained during the process of Manufacturing Example 1 on a glass substrate, (b) the thin film after exposure to light, (c) entire patterns developed on a glass substrate, (d) micropatterns developed on the glass substrate (an enlarged view of (c), scale bar: 200 μm)), (e) entire patterns developed on a silicon wafer, (f) micropatterns developed on the silicon wafer (an enlarged view of (e), scale bar: 200 μm), and (g) entire patterns developed on a PET substrate.

Referring to FIG. 3, it can be confirmed that in both cases in which a glass substrate and a silicon wafer were used as a substrate, micropatterns were satisfactorily formed. In particular, it can be confirmed that, also in the case in which a flexible PET substrate was used, micropatterns were satisfactorily formed.

In addition, although the thin film was colorless in the photograph of (a) a thin film formed on a colorless glass substrate, the patterns appeared blue after exposure to light (b) and after development (c, d). From these results, it can be deduced that the thin film before exposure to light is colorless by containing the diacetylene monomer and the light-exposed regions are blue because the diacetylene monomer is polymerized and thus is converted into polydiacetylene.

Manufacturing Example 3: Pattern Doping

A sulfuric acid solution (1 M, 10 M, or 18 M) was applied to the patterns formed according to Manufacturing Example 1, followed by washing with an ethanol solvent. The washed patterns was dried at 60° C.

FIG. 4 is photographs of (a) entire patterns treated with dilute sulfuric acid (1 M), (b) entire patterns treated with concentrated sulfuric acid (18 M), (c) micropatterns treated with dilute sulfuric acid (1 M) (an enlarged view of (a), scale bar: 200 μm), and (d) micropatterns treated with concentrated sulfuric acid (18 M) (an enlarged view of (c), scale bar: 200 μm), wherein the patterns were obtained according to Manufacturing Example 3.

Referring to FIG. 4, it can be confirmed that in the cases in which the patterns formed on the glass substrate were treated with dilute sulfuric acid (1 M) (a, c), the color of the patterns was changed from blue (see FIGS. 3c and 3d), which was a color before the treatment, to red, but, in the cases in which the patterns were treated with concentrated sulfuric acid (b, d), the color of the patterns were changed from blue, which was a color before the treatment, to colorless. From these results, it can be deduced that, when treated with dilute sulfuric acid (1 M), polydiacetylene main chains contained in the patterns become distorted due to water or sulfuric acid in the dilute sulfuric acid solution, and thus, superpositioned parts of π-orbital arrays in the main chains are partially distorted, which causes a color change to red. In addition, it can be deduced that, when treated with concentrated sulfuric acid (b, d), the polydiacetylene contained in the patterns is decomposed due to sulfuric acid at high concentration, which cause a color change to colorless.

Analysis Example 1: Electrical/Mechanical Properties of Micropatterns

The patterns obtained by treating with the sulfuric acid solution according to Manufacturing Example 3 exhibited an electrical conductivity of 500 to 2000 S/cm. In particular, when treated with concentrated sulfuric acid (18 M), a high electrical conductivity of 1500 to 2000 S/cm was observed. As discussed above, this result was interpreted as occurring because polydiacetylene, which is an insulator, and PSS of PEDOT:PSS were decomposed and removed due to sulfuric acid at high concentration and electrical conductivity was increased due to doping of PEDOT by sulfuric acid ions.

FIG. 5 is graphs illustrating the thicknesses of (a) patterns before addition of a sulfuric acid solution, (b) patterns after addition of a 1 M dilute sulfuric acid, and (c, d) patterns after addition of 18 M concentrated sulfuric acid, wherein the patterns were obtained during the process of Manufacturing Example 3. Here, the thicknesses were measured by means of using Alpha-step.

Referring to FIG. 5, it was confirmed that the pattern thickness was decreased in proportion to the concentration of sulfuric acid (b, c). Such a decrease in thickness is considered to be due to removal of the PSS compound, which is an insulator contained in PEDOT:PSS, as well as of polydiacetylene. In addition, it is considered that electrical conductivity increases in proportion to the decrease in thickness.

FIG. 6 illustrates UV-vis absorption spectra of samples obtained during the process of Manufacturing Examples 1 and 3, and FIG. 7 illustrates transmittance of samples obtained during the process of Manufacturing Examples 1 and 3.

Referring to FIGS. 6 and 7, the samples exhibit a light absorption peak at 620 nm immediately after exposure to light, but, after treating the samples with dilute sulfuric acid (1 M), the samples exhibit a light absorption peak at 480 nm. Accordingly, the color is changed to red. Such a phenomenon was understood as occurring because diacetylene in a sample was changed to polydiacetylene with a π-conjugated main chain due to superposition of π-orbital as a result of exposure to light (blue), and polydiacetylene main chains became distorted due to a dilute sulfuric acid solution so that superpositioned parts of π-orbital arrays in main chains were partially distorted (red). However, it can be confirmed that when the sample is treated with a concentrated sulfuric acid (18 M), a light absorption peak near 500 nm disappears, indicating that polydiacetylene is rapidly decomposed by the concentrated sulfuric acid.

In addition, as shown in FIG. 7, it was confirmed that, when treated with concentrated sulfuric acid, transmittances of the thin films in the visible light region rapidly increased (>90%) due to decomposition of the polydiacetylene molecules. Such a result indicates that the conductive patterns or thin films with excellent conductivity according to the embodiments may be used as a material for transparent electrodes and further, that they may replace ITO, which is currently a commercially available transparent electrode.

Although the present invention has been described in detail with reference to the preferred embodiments, those skilled in the art will appreciate that the scope of the present invention is not limited to the embodiments and that various modifications and changes are possible within the technical spirit and scope of the present invention.

The invention claimed is:

1. A composition for photolithography comprising a water-soluble conductive polymer and a water-soluble diacetylene monomer of the following Formula 1:

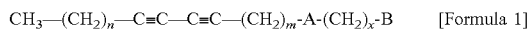  [Formula 1]

wherein n is 2 to 20, m is 2 to 15, and x is 0 to 10,
A is CONH, COO, or CONH—Ar wherein Ar is a phenyl group or a naphthalene group, and when A is CONH—Ar, x is 0,
B is $OSO_3B'$ or $OPO_3B'$, and
B' is H, Li, Na, K, Rb or Cs.

2. The composition of claim 1, wherein the water-soluble conductive polymer is poly(3,4-ethylenedioxythiophene) (PEDOT):poly(styrenesulfonate)(PSS).

3. The composition of claim 1, wherein the compound of Formula 1 is a compound of the following Formula 2:

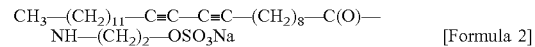  [Formula 2]

4. The composition of claim 2, further comprising water, wherein the water is included in an amount of 10,000 to 50,000 parts by weight based on 100 parts by weight of the water-soluble conductive polymer.

5. The composition of claim 2, wherein the water-soluble diacetylene monomer is included in an amount of 0.01 to 50 parts by weight based on 100 parts by weight of the water-soluble conductive polymer.

6. A method of forming fine patterns comprising:
providing the composition of claim 1;
forming a conductive polymer-containing thin film by coating the composition for photolithography on a substrate; and
forming conductive polymer fine patterns by disposing a photomask on the conductive polymer-containing thin film, irradiating the photomask with ultraviolet light to form a first region, which includes polydiacetylene formed by crosslinking of the diacetylene monomer along with the conductive polymer, and a second region, in which the diacetylene monomer remains due to the photomask blocking ultraviolet light, and selectively removing the second region.

7. The method of claim 6, wherein the substrate is a silicon wafer, a glass substrate, a plastic substrate, a paper, or a metal substrate.

8. The method of claim 6, further comprising doping the conductive polymer fine patterns by applying a dopant of one or more selected from the group consisting of sulfuric acid, sulfonic acid, formic acid, hydrochloric acid, perchloric acid, nitric acid, acetic acid, dimethylformamide (DMF), dimethyl sulfoxide (DMSO), and ethylene glycol.

9. The method of claim 8, wherein the polydiacetylene in the fine patterns is decomposed during the doping step.

10. The method of claim 6, wherein the fine patterns are electrodes for an organic electronic device.

* * * * *